United States Patent [19]

Merrill, deceased et al.

[11] Plant 4,295

[45] Aug. 29, 1978

[54] PEACH TREE

[76] Inventors: Grant Merrill, deceased, late of Red Bluff, Calif., by Lucile B. Merrill, executrix, 325 Breese Ave., Red Bluff, Calif. 96080

[21] Appl. No.: 820,919

[22] Filed: Jul. 29, 1977

[51] Int. Cl.[2] ..... A01H 5/03
[52] U.S. Cl. ..... Plt./43
[58] Field of Search ..... Plt./43

*Primary Examiner*—Robert E. Bagwill
*Assistant Examiner*—James R. Feyrer
*Attorney, Agent, or Firm*—Roger B. Webster

[57] ABSTRACT

A variety of peach tree which is of medium size, medium vigor, spreading, open, vase-formed, and hardy; foliated with medium size, acuminate, lanceolate, acutely pointed, thin, dark green leaves having a crenate, finely serrate margin and a short, thick petiole, and a regular and very productive bearer of uniform, evenly ripening, large-to-medium size, nearly globose or very broadly ovate, semi-freestone fruit having yellow skin substantially overspread with red, and firm, fine, crisp, meaty, yellow flesh streaked with red.

5 Drawing Figures

BACKGROUND OF THE VARIETY

In an extensive plant breeding program, Grant Merrill, originator and now deceased, originated a large number of new and distinct varieties of fruit trees, and which included the herein-claimed variety of peach tree. Such plant breeding program was undertaken in originator's experimental orchard located near Exeter, Tulare County, Calif.

ORIGIN OF THE VARIETY

The present variety of peach tree was originated, in such experimental orchard, as an open-pollinated seedling of an unnamed and unpatented variety of peach tree theretofore produced by originator.

ASEXUAL REPRODUCTION OF THE VARIETY

When such open-pollinated seedling matured as a bearing tree, and it was determined to be of commercial value, the variety was asexually reproduced by grafting on rootstock grown in the aforesaid experimental orchard. The asexual reproductions of the variety ran true to the original tree.

SUMMARY OF THE VARIETY

The herein-claimed new and distinct variety of peach tree is of medium size, medium vigor, spreading, open, vase-formed, and hardy; foliated with medium size, acuminate, lanceolate, acutely pointed, thin, dark green leaves having a crenate, finely serrate margin and a short, thick petiole, and a regular and very productive bearer of uniform, evenly ripening, large-to-medium size, nearly globose or very broadly ovate, semi-freestone fruit having yellow skin substantially overspread with red, and firm, fine, crisp, meaty, yellow flesh streaked with red.

The herein-claimed new and distinct variety of peach tree is further, and more particularly, characterized—in comparison to the Merrill Gem Free peach (U.S. Plant Pat. No. 1,409)—by fruit that ripens at the same time but averages slightly larger in size; the fruit—with fewer split pits—being rounder, more symmetrical, more firm of flesh, and with better shipping quality.

BRIEF DESCRIPTION OF THE DRAWING

The drawing is an illustration, by photographic reproduction in color, of fruit of the variety; certain of the fruit being half cut away to expose the flesh and the stone in the remaining halves.

DESCRIPTION OF THE VARIETY

The botanical details of this new and distinct variety of peach tree—with color definitions (except those in common color terms) referenced to Robert Ridgway's Color Standards and Color Nomenclature (hereinafter identified as "Ridgway") or Maerz and Paul Dictionary of Color (hereinafter identified as "M & P")—are as follows:

TREE

Size: Medium.
Vigor: Medium.
Growth: Upright — spreading.
Density: Open.
Form: Vase-formed.
Hardiness: Hardy.
Production: Very productive.
Bearing: Regular bearer.

TRUNK

Size: Medium.
Texture: Medium.

BRANCHES

Size: Medium.
Texture: Medium.
Color: Brown — Gray.
*Young branches.*—Willow brown (M & P 15-L-7).
*Mature branches.*—Hudson Seal gray (M & P 8-A-9).
Lenticels:
*Number.*—Medium.
Size: Medium.

LEAVES

Size: Medium.
*Average length.*—21.9 cm.
*Average width.*—4.7 cm.

Form: Acuminate. Lanceolate. Acutely pointed.
Thickness: Thin.
Color: Dark green.
*Dorsal side.*—Vorley's green (Ridgway Plate XVIII).
*Ventral side.*—Hellebore green (Ridgway Plate XVII).
Margin: Crenate. Finely serrate.
Petiole: Short — 1-1.5 cm. Thick.
Glands: Average number — 2 to 3. Opposite. Medium size. Reniform. Green. Positioned mostly on blade just below blade; occasionally on base of blade.
Stipules: Small. Linear. Dehiscent.

FLOWER BUDS

Size: Medium.
Length: Medium.
Form: Obtuse. Conic. Plump.
Pubescence: On margin only.

FLOWERS

Blooming period:
*Date of first bloom.*—Mar. 4th, 1977.
*Date of first bloom.*—Mar. 12th, 1977. Medium, as compared with other varieties.
Size: Medium.
*Average length.*—12-14 cm.
*Average width.*—9-11 cm.
Form: Broad — ovate.
Appearance: Non-showy.
Color: Pink (M & P 1-E-4).

FRUIT

Maturity when described: Overripe.
Date of first picking: June 7th, 1976.
Date of last picking: June 17th, 1976.
Size: Large to medium.
*Average diameter axially.*—2 15/16".
*Average transversely in suture plane.*—$2\frac{7}{8}$".
Form: Uniform. Symmetrical. Nearly globose — very broad ovate.
Suture: Distinct. Very shallow. Extends from base to apex. Slight depression beyond pistil point.
Ventral surface: Rounded slightly. Lipped toward apex.
Lips: Equal.
Cavity: Circular to slightly elongated in suture plane, with suture showing on one such side.
*Average depth.*—7/16" to $\frac{1}{2}$".
*Average breadth.*—$\frac{3}{4}$" to $\frac{7}{8}$".
Base: Rounded.
Apex: Short. Rounded. Slight fleshy tip.
Pistil point: Apical.

SKIN

Thickness: Medium.
Texture: Medium.
Tenacity: Tenacious to flesh.
Tendency to crack: None.
Down: Moderate. Medium length.
Color:
*Ground color.*—Antimony yellow (Ridgway Plate XV).
*Blush.*—Pompeian red (Ridgway Plate XIII) to Indian red (Ridgway Plate XVII).

FLESH

Color: Cadmium yellow (Ridgway Plate IV) streaked with red next to skin and throughout.
*Surface of pit cavity.*—Red with yellow fibers.
Amygdalin: Scant.
Texture: Firm. Fine. Crisp. Meaty.
Fibers: Few. Fine. Tender.
Ripens: Evenly.
Flavor: Sub-acid. Mild.
Aroma: Wanting.
Eating quality: Fair to good.

STONE

Type: Semi-free. Parts from flesh smoothly.
Size: Medium.
*Average length.*—$1\frac{3}{8}$"
*Average breadth.*—1"
*Average thickness.*—13/16".
Form: Oval.
Base: Straight.
Hilum: Narrow. Oval.
Apex: Acute.
Sides: Equal. Curved on right and left sides.
Surface: Furrowed near ventral edge and toward apex. Pitted toward base.
Ridges: Jagged. On both sides. Interrupted.
Pits: Elongated.
Ventral edge: Medium, without wing toward base.
Dorsal edge: Narrow, with shallow, narrow groove toward base.
Color: Beige (M & P 12-J-8).
Tendency to split: Slight.

USE

Market.
Dessert.

KEEPING QUALITY

Good.

RESISTANCE TO INSECTS AND DISEASES

Good.

SHIPPING QUALITY

Good.

The peach tree and its fruit herein described may vary in slight detail due to climatic and soil conditions under which the variety may be grown; the present description being of the variety as grown in the Central Valley of Calif.

What is claimed is:

1. A new and distinct variety of peach tree, substantially as illustrated and described, which is of medium size, medium vigor, spreading, open, vase-formed, and hardy; foliated with medium size, acuminate, lanceolate, acutely pointed, thin, dark green leaves having a crenate, finely serrate margin and a short, thick petiole, and a regular and very productive bearer of uniform, evenly ripening, large-to-medium size, nearly globose or very broadly ovate, semi-freestone fruit having yellow skin substantially overspread with red, and firm, fine, crisp, meaty, yellow flesh streaked with red; the variety being more particularly characterized-in comparison to the Merrill Gem Free peach—by fruit that ripens at the same time but averages slightly larger in size; the fruit—with fewer split pits—being rounder, more symmetrical, more firm of flesh, and with better shipping quality.

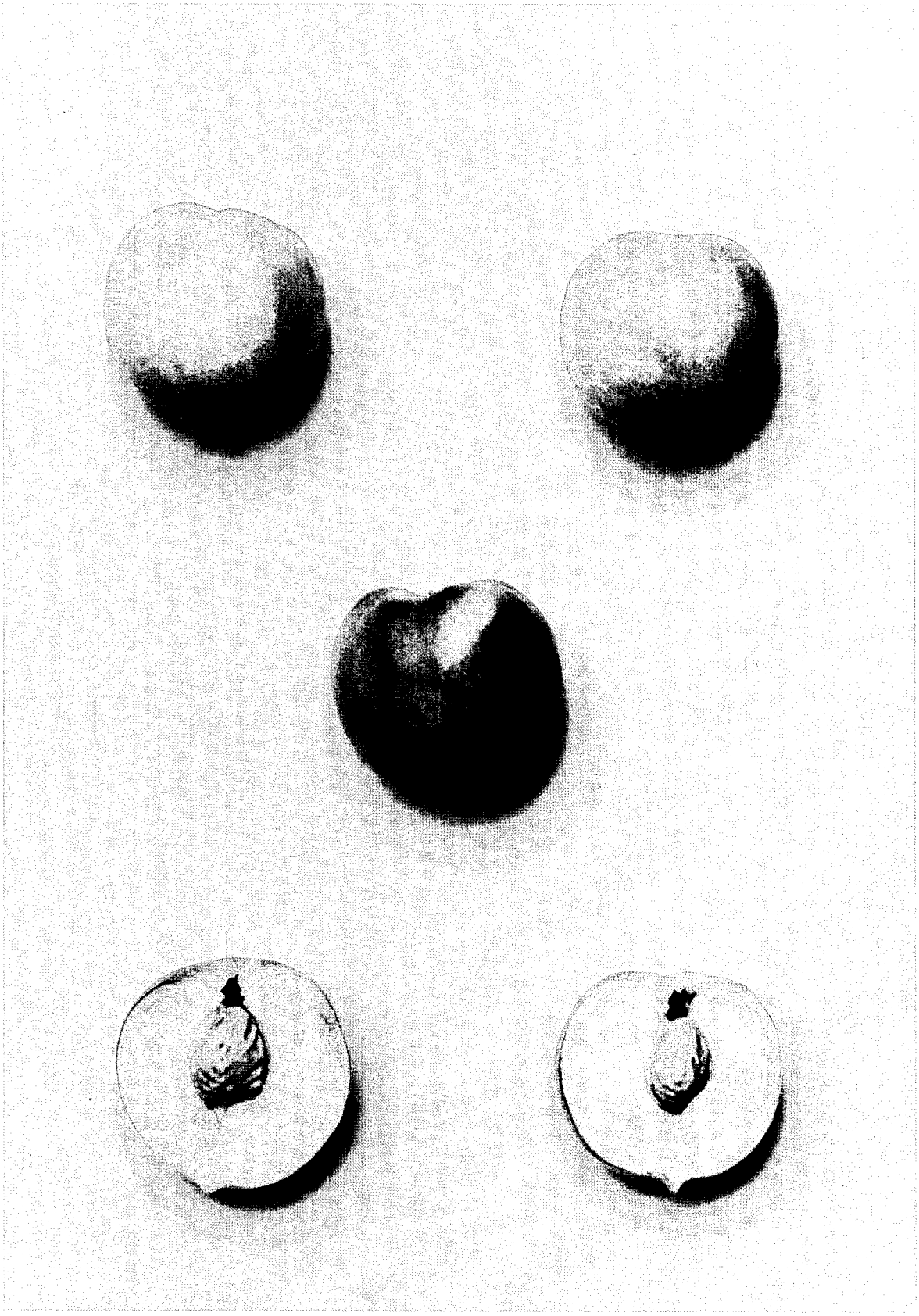

* * * * *